US010683336B2

(12) United States Patent
Blankenstein et al.

(10) Patent No.: US 10,683,336 B2
(45) Date of Patent: Jun. 16, 2020

(54) TUMOR SPECIFIC T-CELL RECEPTORS

(71) Applicant: MAX-DELBRUECK-CENTRUM FUER MOLEKULARE MEDIZIN (MDC) BERLIN-BUCH, Berlin (DE)

(72) Inventors: Thomas Blankenstein, Berlin (DE); Gerald Willimsky, Berlin (DE)

(73) Assignee: Max-Delbrüeck-Centrum Für Molekulare Medizin (MDC) Berlin-Buch, Berlin (DE)

( * ) Notice: Subject to any disclaimer, the term of this patent is extended or adjusted under 35 U.S.C. 154(b) by 0 days.

(21) Appl. No.: 14/648,314

(22) PCT Filed: Nov. 29, 2013

(86) PCT No.: PCT/EP2013/075141
§ 371 (c)(1),
(2) Date: May 29, 2015

(87) PCT Pub. No.: WO2014/083173
PCT Pub. Date: Jun. 5, 2014

(65) Prior Publication Data
US 2015/0307585 A1    Oct. 29, 2015

Related U.S. Application Data

(60) Provisional application No. 61/731,666, filed on Nov. 30, 2012.

(30) Foreign Application Priority Data

Nov. 30, 2012  (GB) .................................. 1221628.9

(51) Int. Cl.
*C07K 14/725* (2006.01)
*C07K 14/47* (2006.01)
*A61K 39/00* (2006.01)
*A61K 38/00* (2006.01)

(52) U.S. Cl.
CPC ...... *C07K 14/7051* (2013.01); *A61K 39/0011* (2013.01); *C07K 14/4748* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 9,113,616 B2* | 8/2015 | MacDonald | A01K 67/0278 |
| 9,505,824 B2* | 11/2016 | Sasada | A61K 39/0011 |
| 2003/0093818 A1* | 5/2003 | Belmont | A01K 67/0275 |
| | | | 800/4 |
| 2008/0219956 A1* | 9/2008 | Russell | A61K 35/28 |
| | | | 424/93.7 |
| 2011/0293637 A1* | 12/2011 | Hacohen | C12Q 1/6886 |
| | | | 424/173.1 |

FOREIGN PATENT DOCUMENTS

| | | | | |
|---|---|---|---|---|
| CN | 102574906 A | | 7/2012 | |
| WO | WO-2007017201 A1 | * | 2/2007 | ........... C12N 5/0636 |
| WO | WO-2007034489 A2 | * | 3/2007 | ......... A61K 39/0008 |
| WO | WO 2011/001152 A1 | | 1/2011 | |
| WO | WO 2012/038055 A1 | | 3/2012 | |

OTHER PUBLICATIONS

Popovic et al. (Blood. 2011; 118(4):946-954).*
Janeway et al., Immunobiology, 5th Ed., Garland Science, pp. 106-108 and 260-263, (2001).*
Garcia et al., Cell, vol. 122, 333-336, Aug. 12, 2005.*
Portolano et al., J Immunol. Feb. 1, 1993;150(3):880-7.*
Kvistborg et al. (OncoImmunology 1:4, 409-418; Jul. 2012).*
Morgan et al. (Molecular Therapy vol. 18 No. 4, 843-851, 2010).*
Johnson et al. (Blood. 2009;114:535-546).*
Parkhurst et al. (Mol Ther. Mar. 2011;19(3):620-6).*
Li et al. (Nat Med. Sep. 2010;16(9):1029-34).*
Krauthammer et al. 2012 (Nature Genetics, vol. 44, No. 9, pp. 1006-1014 and Supplemental pages independently numbered 1-43).*
Faden et al., Hastings Cent Rep. Nov.-Dec. 2003;33(6):13-27 (Year: 2003).*
Woodsworth et al., Genome Medicine 2013, 5:98. (Year: 2013).*
Robins et al., Blood. 2009;114:4099-4107. (Year: 2009).*
Subbramanian et al. (Nat Biotechnol. Nov. 2004;22(11):1429-34). (Year: 2004).*
Memorandum of Feb. 22, 2018, 2 pages (Year: 2018).*
Manning et al., Immunity, vol. 8, 413-425, Apr. 1998. (Year: 1998).*
Houghton, A. N., Guevara-Patiño, J. A., "Immune recognition of self in immunity against cancer." *The Journal of Clinical Investigation*, Aug. 2004, 114(4): 468-471.
Machesky, L. M., Sansom, O. J., "Rac1 in the driver's seat for melanoma." *Pigment Cell Melanoma Res.*, Nov. 2012, 25: 762-764.
Wei, Xiaomu, et al., "Exome sequencing identities GRIN2A as frequently mutated in melanoma." Nature Genetics, May 2011, 43(5): 442-448.
Popović, Jelena. "Suitability of the TEL-AML1 chromosomal translocation for targeting by adoptive T cell therapy of leukemia." Diss. Freie Universität Berlin, Aug. 2011, 1-93.
Database EMBL [Online] Feb. 20, 1998 (Feb. 20, 1998), "*Mus musculus* (house mouse) partial T cell receptor beta chain," XP002719327, retrieved from EBI accession No. EMBL: AACO2863 Database accession No. AACO2863.

(Continued)

Primary Examiner — Zachary S Skelding
(74) Attorney, Agent, or Firm — Saliwanchik, Lloyd & Eisenschenk

(57) ABSTRACT

The present invention relates to a method for the production of novel T-cell receptors (TCR) which provide a reduced risk of adverse events in immune therapy, specifically in adoptive T cell transfer. The TCRs produced according to the method of the invention are specific for tumor cells and do not react with healthy tissue. Furthermore provided are nucleic acids encoding the TCR of the invention, vectors and host cells comprising the TCRs of the invention as well as their use is the treatment of tumorous diseases.

4 Claims, 1 Drawing Sheet
Specification includes a Sequence Listing.

(56) References Cited

OTHER PUBLICATIONS

Database Geneseq [Online] Nov. 13, 2008 (Nov. 13, 2008), "Human T-cell receptor CDR3 peptide, SEQ ID 2592," XP002719263, retrieved from EBI accession No. GSP: ATF88948 Database accession No. ATF88948 & EP 2 116 596 A1 (Int Inst Cancer Immunology Inc [JP]) Nov. 11, 2009 (Nov. 11, 2009).
Hanson, Holly L. et al., "Eradication of Established Tumors by CD8+T Cell Adoptive Immunotherapy," *Immunity*, Aug. 2000, 13:265-276.
Hodis, Eran et al., "A Landscape of Driver Mutations in Melanoma," *Cell*, Jul. 2012, 150:251-263.
Kerkar, Sid P. et al., "Tumor-specific CD8+T cells expressing IL-12 eradicate established cancers in lymphodepleted hosts," *Cancer Res.*, Sep. 2010, 70(17):6725-6734.
Krauthammer, Michael et al., "Exome sequencing identifies recurrent somatic RAC1 mutations in melanoma," *Nat Genet.*, Sep. 2012, 44(9):1006-1014.
Li, Liang-Ping et al., "Transgenic mice with a diverse human T cell antigen receptor repertoire," *Nature Medicine*, Sep. 2010, 16(9):1029-1035.
Morris, Emma et al., "Generation of tumor-specific T-cell therapies," *Blood Reviews*, 2006, 20:61-69.
Offringa, Rienk. "Antigen choice in adoptive T-cell therapy of cancer," *Current Opinion in Immunology*, 2009, 21:190-199.
Restifo, Nicholas P. et al., "Adoptive immunotherapy for cancer: harnessing the T cell response," *Nature Reviews: Immunology*, Apr. 2012, 12:269-281.
Robbins, Paul F. et al., "A Mutated β-Catenin Gene Encodes a Melanoma-specific Antigen Recognized by Tumor Infiltrating Lymphocytes," *J. Exp. Med.*, Mar. 1996, 183:1185-1192.
"Human NY-ESO-1 specific T cell receptor (TCR) beta chain, SEQ ID 31," XP002719262, retrieved from EBI accession No. GSP:AZU40602, Database accession No. AZU40602 sequence.

\* cited by examiner

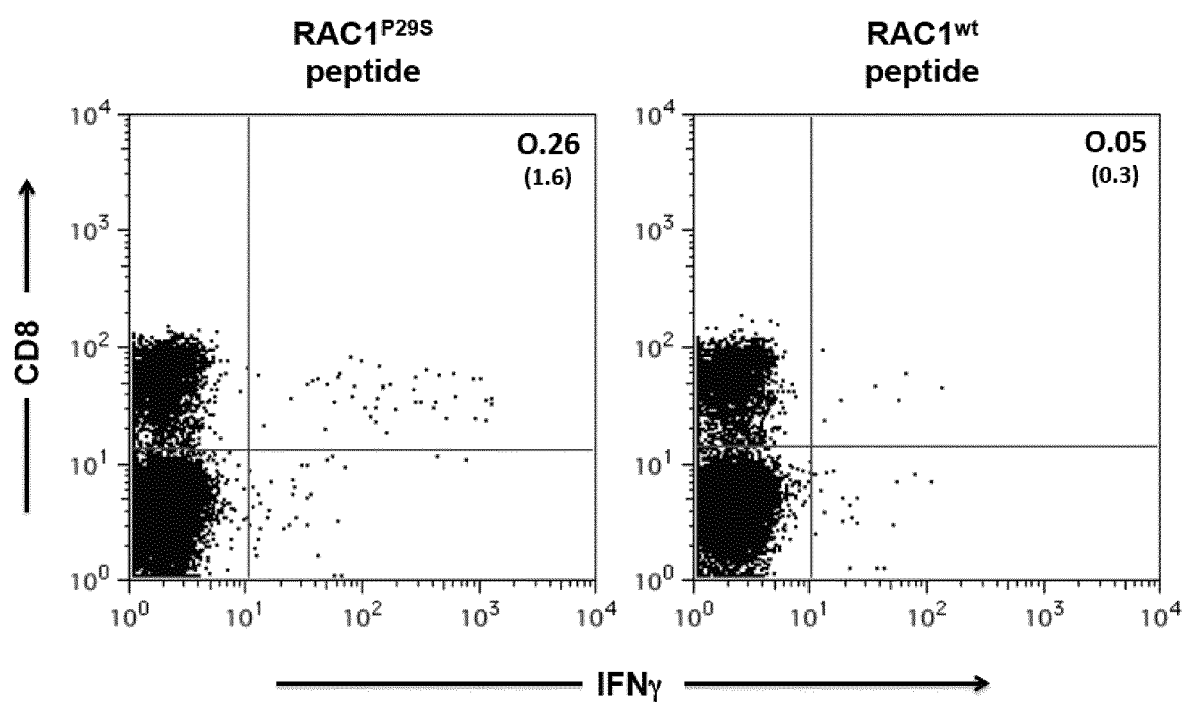

TUMOR SPECIFIC T-CELL RECEPTORS

CROSS REFERENCE TO A RELATED APPLICATION

This application is a National Stage Application of International Application Number PCT/EP2013/075141, filed Nov. 29, 2013; which claims priority to Great Britain Application No. 1221628.9, filed Nov. 30, 2012 and claims the benefit of U.S. Provisional Application Ser. No. 61/731, 666, filed Nov. 30, 2012; all of which are incorporated herein by reference in their entirety.

The Sequence Listing for this application is labeled "SeqList-07Oct17-ST25.txt", which was created on Oct. 7, 2017, and is 27 KB. The entire content is incorporated herein by reference in its entirety.

FIELD OF THE INVENTION

The present invention pertains to a method for the production of novel T-cell receptors (TCR) which provide a reduced risk of adverse events in immune therapy, specifically in adoptive T cell transfer. The TCRs produced according to the method of the invention are specific for tumor cells and do not react with healthy tissue. Furthermore provided are nucleic acids encoding the TCR of the invention, vectors and host cells comprising the TCRs of the invention as well as the use of these compounds in the treatment of tumorous diseases.

DESCRIPTION

Despite remarkable technological advancements in the diagnosis and treatment options available to patients diagnosed with cancer, the prognosis still often remains poor and many patients cannot be cured. Immunotherapy holds the promise of offering a potent, yet targeted, treatment to patients diagnosed with various tumors, with the potential to eradicate the malignant tumor cells without damaging normal tissues. In theory the T cells of the immune system are capable of recognizing protein patterns specific for tumor cells and to mediate their destruction through a variety of effector mechanisms. Adoptive T-cell therapy is an attempt to harness and amplify the tumor-eradicating capacity of a patient's own T cells and then return these effectors to the patient in such a state that they effectively eliminate residual tumor, however without damaging healthy tissue. Although this approach is not new to the field of tumor immunology, still many drawbacks in the clinical use of adoptive T cell therapy impair the full use of this approach in cancer treatments.

A TCR is a heterodimeric cell surface protein of the immunoglobulin super-family which is associated with invariant proteins of the CD3 complex involved in mediating signal transduction. TCRs exist in $\alpha\beta$ and $\gamma\delta$ forms, which are structurally similar but have quite distinct anatomical locations and probably functions. The extracellular portion of native heterodimeric $\alpha\beta$TCR consists of two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. The use of TCR gene therapy overcomes a number of current hurdles. It allows equipping patients' own T cells with desired specificities and generation of sufficient numbers of T cells in a short period of time, avoiding their exhaustion. The TCR will be transduced into central memory T cells or T cells with stem cell characteristics, which may ensure better persistence and function upon transfer. TCR-engineered T cells will be infused into cancer patients rendered lymphopenic by chemotherapy or irradiation, allowing efficient engraftment but inhibiting immune suppression. Transgenic mice expressing human MHC molecules and a diverse human TCR repertoire serve as a tool to rapidly analyze whether peptide antigens are immunogenic, i.e. are they efficiently processed and presented by MHC molecules, do they efficiently induce T cell responses following immunization (Li et al. 2010 Nat Med).

Using the human TCR transgenic mouse, any human peptide sequence not encoded by the mouse genome is suitable for immunization and will yield TCRs with optimal affinity. Optimal affinity means that the T cells are restricted to human self-MHC molecules and recognize the peptide antigen as foreign, e.g. represent the non-tolerant repertoire. By using peptide/MHC multimers, specific T cells of the transgenic mice can be sorted, human TCRs isolated, e.g. by single cell PCR, the TCRs optimized for efficient expression while avoiding mispairing with endogenous TCR and used for transduction of patients' T cells with viral vectors (Uckert et al. 2008 Cancer Immunol Immunother; Kammertoens T et al. 2009 Eur J Immunol).

The key problem of ATT is to target the right antigen to prevent tumor recurrence and toxic side effects. This sounds simple given the large number of putative tumor antigens. However, most are tumor-associated (self) antigens (TAAs). TAAs are also expressed by normal cells. Expression by rare but vital cells has usually not been analyzed. Moreover, TAA expression may be heterogeneous within the tumor/metastases of a given individual. Thus, targeting TAAs bears the risk of ineffective long-term responses and destruction of normal tissues.

Clinical trials with TCR (or chimeric antibody receptor; CAR)-engineered T cells, e.g. directed against Melan-A/MART-1, gp100, HER-2 and carcinoembryonic antigen, support this assumption. Morgan R A and colleagues present a case report on a patient with ERBB2 overexpressing cancer that was treated by infusing T cells transduced with a chimeric antigen receptor recognizing ERBB2 into the patient. After 15 minutes of the infusion the patient experienced respiratory distress and dramatic pulmonary infiltrate. The patient died after 5 days. This dramatic outcome underlines the problem of toxic adverse effects in the context of adoptive T cell therapy.

Another approach makes use of the immunization of mice, the subsequent isolation of the T-cells and T cell receptors from these cells, in order to transduce autologous peripheral lymphocytes of a tumor patient. The transduced lymphocytes were expanded and then re-infused. Although tumor regression was observed, the patients still showed the destruction of normal cells (Johnson L A et al. 2009 Blood).

Parkhurst and colleagues (2010 Mol Ther) genetically engineered autologous T lymphocytes of patients suffering from metastatic colorectal cancer refractory to standard treatments. The T lymphocytes were altered to express a murine T cell receptor directed at the carcinoembryonic antigen (CEA). Again the report shows regression of the tumor, however with severe transient inflammatory colitis as side effect in all patients.

Thus, for many, if not most, tumor associated antigens substantial toxicity by effective adoptive T cell therapy is predictable.

In view of the above described major drawbacks in the background art, it is the objective of the present invention to provide novel approaches for adoptive T-cell therapy which can overcome the severe side effects observed in immune therapy when genetically engineered T cell receptors are introduced into autologous lymphocytes and re-infused into a human patient. A more specified object of the present invention is to provide novel antigen recognizing constructs which specifically target tumor cells and not healthy cells.

In a first aspect of the present invention, the above objective is solved by a method for the production of a human T cell receptor (TCR) or a T-cell, which is specific for tumorous cells and has reduced adverse effects in adoptive T-cell therapy, comprising the method steps of a. Providing a host organism expressing un-rearranged human TCR loci,
b. Immunizing said host organism with a peptide comprising an epitope specific for a tumor specific antigen (TSA),
c. Isolating from said host organism or cell a T cell clone having an activity against said human mutated TSA,
d. Optionally, isolating from said T cell clone the TCR, wherein said TSA is selected out of the class of somatic mutated antigens.

The surprising finding of the present invention is that if, by contrast to the state of the art approaches, mutant cancer-driving oncogenes, specifically TSAs out of the class of somatic mutated antigens, are targeted by adoptive T cell therapy (ATT), many of the problems with TAAs as known in the state of the art are resolved. Except for antigens encoded by cancer viruses, mutated antigens are the only exclusively tumor-specific antigens.

Of course, the TCRs produced in accordance with the herein described method of the invention do not only provide their advantageous effects in adoptive T cell therapy, but also in any other therapeutic approach wherein the specific binding of the TCR to its target is employed.

The TCRs isolated in accordance with the method of the present invention are advantageous over the state of the art antigen recognizing constructs due to their reduced risk for adverse effects which are observed in adoptive T cell therapy. Adverse effects in context of adoptive T cell transfers are mainly due to autoimmune reactions or to off-target reactions. The present invention specifically intends to solve the former problem by providing T cells which are highly specific to tumor cells and do not mediate an immune reaction against a patient's healthy tissue. Adverse events following infusion of human autologous or allogeneic lymphocytes that the present invention seeks to reduce can be various. In a preferred embodiment of the present invention the TCR obtained by the present invention provide a reduced risk when used in adoptive T cell therapy for inducing healthy tissue damage, which might result in edema and necrosis.

In one preferred embodiment of the present invention said host organism further comprises a transgene for the expression of a human major histocompatibility complex (MHC) class I or II allele. Preferably the MHC is a human leucocyte antigen (HLA) type which is known or suspected to be able to present said mutated TSA. Even more preferred is that the HLA type which is expressed in said host organism is known or suspected to be able to present a peptide derived from said mutated TSA. This peptide should comprise an amino acid sequence including the mutation which is specifically present in the mutated TSA opposed to the corresponding un-mutated (wild type) version of the same protein.

HLAs corresponding to MHC class I comprise the types A, B, and C. HLA class I complexes present peptides which are processed inside the presenting cell (including alien peptides' such as viral peptides if present). In general, such HLA class I peptides are small polymers, about 9 amino acids in length. HLAs corresponding to MHC class II comprise the types DP, DM, DOA, DOB, DQ, and DR. HLA class II complexes present antigens originating from the outside of the cell. They can be of a length between 12 and 18 amino acids. The characterization of the responsible HLA alleles presenting an antigen of choice is a methodology generally known in the art.

In said host organism used in accordance with the present invention insofar it is not a human the un-rearranged human TCR loci are preferably present as one or more transgenes in the genome of said host organism. Preferably these loci encode TCR α and β chains, and preferably comprise a plurality, ideally all, of human TCR V, D, J, and/or C genes.

For the method in accordance with the present invention it is preferably a prerequisite that said host organism has an adaptive immune system and/or is able to mount a VDJC rearrangement within said human TCR loci. Furthermore a host organism is preferred which is able to express heterologous TCRs. In certain preferred embodiments of the invention said host organism is a transgenic animal, preferably a mammal, more preferably a non-human mammal, most preferably a mouse, a rat, a donkey, a rabbit, a hare or a monkey, or any animal which is known in the art to be a host for the generation of T-cells.

In the context of such embodiments of the invention which relate to the above method and wherein non-human host organisms are used, such a non-human host organism preferably further comprises inactivated endogenous TCR loci, preferably wherein said endogenous TCR loci encode for the TCR α and β chains of said non-human host organism.

In one very specific embodiment of the present invention said host-organism is an "ABabDII" mouse. The term "ABabDII" mouse refers to the transgenic animal produced as described in Li et al., 2010; 16:1029-34 Nature Medicine. Of course it is understood that also any other transgenic animal produced with the same methodology as described in Li et al. shall be encompassed as a suitable host organism for use in the herein described embodiments of the invention.

An alternative embodiment relates to a method, wherein a human, for example a healthy individual or a human patient suffering from a tumorous disease, is immunized with said peptide as described herein. In this embodiment T cells can be isolated subsequent to the immunization process from the blood of the human subject. This embodiment has the advantage that the improved T cell receptor is expressed on human, ideally autologous, T cells which can then be used for reinfusion in adoptive T cell therapy.

The peptide used for the immunization of the host organism in context of the method of the present invention comprises an amino acid sequence which is in at least one amino acid residue mutated compared to the amino acid sequence of the corresponding wild-type cellular protein. The present invention relates to the use of tumor specific antigens, therefore proteins which were mutated in the development of tumor cells and thus in this specific mutated form exclusively are present in tumor cells. Normal, healthy, cells however might still express the original un-mutated (wild type) protein. Thus, for the herein described invention it is specifically preferred that the peptide used for immunization comprises in its sequence the mutation which differentiates the TSA from the original un-mutated cellular protein. Preferred peptides for use in the method of the invention comprise any of the sequences shown in SEQ ID No. 1 to 27. In preferred embodiments of the invention the peptide for immunization comprises the amino acid sequence shown in SEQ ID No. 1.

Antigens which are specifically expressed in tumor cells and not in healthy tissue can be categorized into four types: (I) mutated antigens develop during tumor-genesis by point mutations or translocations within the tumor cells. Those antigens are strictly tumor-specific. In the context of the invention these antigens are referred to as tumor specific antigens (TSA). (II) cancer/germline antigens are usually expressed solely within the germ cells of an adult organism and not in healthy somatic tissue. In cancer cells, however, due to the loss of epigenetic regulation, germ-cell specific genes can be activated. (III) differentiation antigens are expressed in tumors and their healthy progenitor cells. CTL responses against such antigens often result in auto-immune reactions. (IV) overexpressed TAA show only minor expression in healthy cells whereas in a tumor those antigens are strongly activated. For the present invention it is preferred that only antigens of the first type are used.

For the invention TSAs formed by any kind of mutation are comprised. For merely illustrative reasons the following types of mutations are described: amino acid substitution, deletion, addition, insertion, or chemical or post-translational modification. Furthermore included are chromosomal translocations and exclusively in tumor cells expressed splice variants, for example which occur by unspecific splicing mutations resulting in new splice sites.

For the immunization process said peptide can have any length. A minimum requirement is however the presence of the epitope containing the above mentioned mutated sequence. Preferred peptides of the invention have a length of 100 amino acids, preferably of 50 amino acids, more preferably of 30 amino acids, even more preferably 8 to 16 amino acids. The exact peptide length might vary depending on whether the TSA is MHC class I or MHC class II presented.

In order to enhance immunization of the host organism, it is preferred that an adjuvant is used together with the peptide. An adjuvant is for example, without being limiting thereto, CpG and/or incomplete Freunds adjuvant. After the initial immunization with the peptide, said host organisms is treated preferably at least one or two, three or four more times with said peptide and/or the adjuvant of choice. Freund's adjuvant is a solution of (mineral) oil wherein the antigen for immunization is emulsified. Incomplete Freund's adjuvant, as preferably used in this invention, does not contain any mycobacterial components.

During and after the immunization process said host-organism should develop T cells expressing rearranged T cell receptors specific against the TSA of the invention. Such T-cell clones are then in a preferred embodiment isolated from said host organism. For example the cells can be isolated from spleen cells, lymph node cells or blood. T cell clones are selected for example via the surface expression of CD4 or CD8, depending on whether the TSA epitope is MHC class I or II. Methods for the isolation of single T cell clones form host organisms are well known for the person of skill in the art. The present invention is not restricted to a specific methodology for isolating T cells. However, in one preferred embodiment of the invention, said T cells or said T cell clone is after isolation further tested for the expression of a TCR binding to the TSA used in the method of the invention. This is preferably done by tetramer binding (staining) using TSA specific HLA tetramers. Optionally, the isolated T cell or T cell clone is also tested for its specificity to the TSA compared with the un-mutated version of the cellular protein. To this end, T cell reactivity against peptides comprising the mutation and against peptides comprising the wild-type version is compared. In a preferred embodiment such T cells or T cell clones are isolated in accordance with the method of the invention, which are highly selective for the TSA and not the un-mutated version of the cellular protein.

Another embodiment of the invention relates to a method as described herein, where after isolation of the T cell or T cell clone, the TCR sequence is cloned. In this embodiment the method in step d. as described above, comprises the further method steps of (i) preparing cDNA from said T-cell clone, and (ii) amplifying said cDNA, and (iii) cloning the respective TCR α and β genes into a vector. Preferably a retroviral vector for the transduction of human peripheral blood lymphocytes is used as a vehicle for the TCR of the invention. Means and methods for such a cloning procedure are well known to the skilled person.

In another preferred embodiment of the invention the TSA used is expressed in a tumor cell or tumor disease.

As used herein, the term "tumor" or "tumor disease" means both benign and malignant tumors or neoplasms and includes melanomas, lymphomas, leukemias, carcinomas and sarcomas. Illustrative examples of tumor tissues are cutaneous such as malignant melanomas and mycosis fungoides; hematologic tumors such as leukemias, for example, acute lymphoblastic, acute myelocytic, or chronic myelocytic leukemia; lymphomas such as Hodgkin's disease or malignant lymphoma; gynecologic tumors such as ovarian and uterine tumors; urologic tumors such as those of the prostate, bladder, or testis; soft tissue sarcomas, osseus, or nonosseous sarcomas, breast tumors; tumors of the pituitary, thyroid, and adrenal cortex; gastrointestinal tumors such as those of the esophagus, stomach, intestine, and colon; pancreatic and hepatic tumors; laryngeae papillomestasas and lung tumors. Preferred tumors in the context of the present invention are selected from melanoma, lung tumor, endometrial tumors, glioma, lymphoma, leukemia or prostate tumor.

Exemplary TSAs which can be subject to the inventive method described herein—without being limiting for the invention—are described in Krauthammer et al. 2012 (Nature Genetics). A preferred selection of TSAs which are presented by HLA type A2 are RAC1, RAC2, RHOT1, MAP2K1, MAP2K2, Nos1, EGFR, SMCA4, STK11, ARID1A, RBM10, U2AF1, EP300, CHD4, FBXW7, H3F3A, KLHL6, SPOP, or MED12. Their respective mutated epitope sequences are provided in the examples section herein below.

The object of the present invention is furthermore solved by a nucleic acid molecule encoding for a TCR obtained or obtainable by the method in accordance with the present invention. Furthermore provided in the present invention are nucleic acid molecules which encode for the respective a α or β chains of an TCR of the invention, or for a variable or constant domain of a TCR of the invention, or for a fragment of a TCR of the invention, preferably wherein such a fragment of the TCR still has the activity/ability for binding its TSA. In addition to that, the nucleic acid molecule optionally has further sequences which are necessary for protein expression of the nucleic acid sequence, specifically for an expression in a mammalian/human, most preferably an immune cell. The nucleic acid used can be contained in a vector suitable for allowing expression of the nucleic acid sequence corresponding to the TCR in a cell.

Also provided is a vector or a cell comprising a nucleic acid molecule described herein above, specifically wherein the vector is for use in medicine. Also a cell comprising a vector according to the invention is provided.

In another aspect the invention provides the T-cell receptor (TCR), or a fragment thereof, as obtained or obtainable by the method of the present invention. In this context it is specifically preferred that the TCR of the invention is a TCR which shows reduced adverse effects in immune therapy. The TCR of the invention preferably does not target healthy cells or tissue, which express the un-mutated (wild-type) version of the TSA used for the generation of the TCR. The TCR of the invention in preferred embodiments does not induce necrosis events, and does not mount when given to subject an immune response against healthy cells or tissue. preferred TCR of the invention is a TCR specific for the epitope shown in SEQ ID No. 1.

Preferably a TCR in accordance to the invention may be a TCR as described herein below.

Yet another embodiment of the invention pertains to a single chain TCR (scTCR, preferably an αβ-scTCR, which are derived from a sequence of a TCR of the present invention. Singlechain TCRs (scTCRs) are artificial constructs consisting of a single amino acid strand. An scTCR can comprise a polypeptide of a variable region of a first TCR chain (e.g., an [alpha] chain) and a polypeptide of an entire (full-length) second TCR chain (e.g., a [beta] chain), or vice versa. Furthermore, the scTCR can optionally comprise one or more linkers which join the two or more polypeptides together. The linker can be, for instance, a peptide which joins together two single chains, as described herein.

Also provided is such a scTCR of the invention or other TCR derived molecule of the invention, which is fused to a human cytokine, such as IL-2, IL-7 or IL-15. TCRs of the present invention can also be provided as a multimeric complex, comprising at least two scTCR or TCR molecules, wherein said scTCR or TCR molecules are interconnected for example by an introduced biotin-streptavidin functionality.

In another aspect of the present invention a host cell is provided, comprising a vector a nucleic acid or a TCR molecule as described herein above. In preferred embodiments of the invention the host cell is a human cell, preferably a human T-lymphocyte, which is positive for the expression of CD4 or CD8. Such a host cell of the invention is preferably obtained by transduction of a nucleic acid or vector in accordance with the present invention. Transduction methods for introducing nucleic acid molecules into T cells are well known in the art and include without being limiting thereto viral transduction vehicles.

In an alternative aspect of the invention a T-cell is provided obtained or obtainable by a method for the production of a human T cell receptor (TCR), which is specific for tumorous cells and has reduced adverse effects in adoptive T-cell therapy as described herein above. Such a T cell is depending on the host organism used in the method of the invention for example a human or non-human T-cell, preferably a non-human T-cell expressing a human TCR.

The provided compounds of the invention are in a further aspect for use in medicine, for example for use in the treatment of a cancerous disease, specifically wherein the cancerous disease is characterized by the specific expression of said mutated TSA. Most preferably the compounds of the invention are used in a cancer treatment that involves an adoptive T-cell transfer.

Yet another aspect of the invention relates to a method of treating a human subject, specifically human subject suffering from a tumor disease. The method of treatment comprises the administration of any of the aforementioned compounds into a patient in need of such a treatment. The administration of the compounds of the invention can for example involve the infusion of T cells of the invention into said patient. Preferably such T cells are autologous T cells of the patient which were in vitro transduced with a nucleic acid or TCR of the present invention.

Thus also provided is a pharmaceutical composition, comprising a TCR or TCR fragment according to the invention, or a nucleic acid, a vector, a host cell, or an isolated T cell according to the invention. In a preferred embodiment the pharmaceutical composition is for immune therapy.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Tumor antigens that are preferably used in the methods of the present invention to obtain a TCR of the invention are listed in tables 1 and 2 below (the mutation is indicated as amino acid exchange within the epitope in brackets):

TABLE 1

| Gene | Protein | Epitope |
| --- | --- | --- |
| Rac1 | Ras-related C3 botulinum toxin substrate 1 | 27-35 (P29S) |
| TRRAP | transformation/transcription domain-associated protein | 715-723 (S722F) |
| Rac2 | Ras-related C3 botulinum toxin substrate 2 | 28-36 (P29L) |
| | | 28-36 (P29Q) |
| Nos1 | Nitric oxide synthase | 770-779 (S771L) |
| ARID1A | AT-rich interactive domain-containing protein 1A | 1999-2007 (E2000V) |
| | | 1021-1031 (W1022L) |
| H3F3A | Histone H3.3 | 28-36 (G34V) |
| KLHL6 | Kelch-like protein 6 | 48-56 (F49L) |
| ID3 | Inhibitor of DNA binding 3 | 50-58 (L54V) |
| FLT3 | Fms-related tyrosine kinase 3 | 835-843 (D835Y) |
| | | 835-843 (D835V) |
| FBXW7 | F-box/WD repeat-containing protein 7 | 456-464 (F462S) |
| | | 456-464 (A463T) |
| Med12 | Mediator of RNA polymerase II transcription subunit 12 | 724-732 (D727E) |
| CDK12 | Cyclin-dependent kinase 12 | 898-906 (Y901C) |
| CDC42 | Cell division cycle 42 | 7-14 (G12V) |
| SMARCA4 | SWI/SNF related, matrix associated, actin dependent regulator of chromatin, subfamily a, member 4 | 1153-1161 (G1159W) |

TABLE 1-continued

| Gene | Protein | Epitope |
|---|---|---|
| SMO | Smoothened, frizzled family receptor | 412-420 (L412F) |
| SF3B1 | Splicing factor 3b, subunit 1 | 693-701 (K700E) |
| CHD4 | Chromodomain-helicase-DNA-binding protein 4 | 907-916 (L912V) |
| SPOP | Speckle-type POZ protein | 83-91 (Y87N) |
|  |  | 83-91 (Y87C) |
| MAP2K2 | Dual specificity mitogen-activated protein kinase2 | 154-162 (S154F) |
| Notch1 | Notch1 | 1568-1576 (L1574P) |
|  |  | 1592-1600 (R1598P) |
| FOXA1 | Forkhead Box A1 | 221-229 (D226N) |
| 2$^{nd}$ NT5C2 | 5'-Nucleotidase, Cytosolic II | a) 233-241 |
|  |  | b) 236-244 (R238L) |
| 2$^{nd}$ Bcr-Abl | Bcr-Abl | 247-255 (E255K) |
| RHOT1 | Mitochondrial Rho GTPase 1 | 29-37 (P30L) |
| MAP2K1 | Dual specificity mitogen-activated protein kinase1 | 20-28 (E20K) |
| EGFR | Epidermal growth factor receptor | 717-725 (G719A) |
|  |  | 1125-1133 (H1129Y) |
| STK11 | Serine/threonine-protein kinas | 219-228 (P221L) |
| RBM10 | RNA-binding protein 10 | 316-324 (I316F) |
| U2AF1 | Splicing factor U2AF 26 kDa subunit | 28-36 (S34F) |
| EP300 | Histone acetyltransferase p300 | 1623-1631 (R1627W) |
| CDK4 | Cyclin-dependent kinase 4 | 23-32 (R24C) |
|  |  | 23-32 (R24L) |
| PPP6C | Protein phosphatase 6, catalytic subunit | 269-277 (S270L) |
| TACC1 | Transforming, acidic coiled-coil containing protein 1 | 792-801 (C794F) |
| KRAS | V-Ki-ras2 Kirsten rat sarcoma viral oncogene homolog | 5-14 (G12V) |
| TRAF7 | TNF receptor-associated factor 7, E3 ubiquitin protein ligase | 518-527 (N520S) |
|  |  | 531-541 (G536S) |
| HIST1H3B | Histone cluster 1, H3b | 26-35 (K27M) |
| ALK | Anaplastic lymphoma receptor tyrosine kinase | 1272-1280 (R1275Q) |
| ABL1 | C-abl oncogene 1, non-receptor tyrosine kinase | 251-260 (E255K) |
|  |  | 247-255 (E255V) |
| CBL | Cbl proto-oncogene, E3 ubiquitin protein ligase | 398-406 (H398Y) |
| NPM1 | Nucleophosmin (nucleolar phosphoprotein B23, numatrin) | 283-291 (c.863_864insTCTG Insertion) |
|  |  | 283-291 (c.863_864insCATG Insertion) |
|  |  | 283-291 (c.863_864insCATG Insertion) |
| EZH2 | Enhancer of zeste homolog 2 | 637-645 (Y641F) |
| GNAS | GNAS complex locus | 201-210 (R201C) |
| PDGFRA | Platelet-derived growth factor receptor, alpha polypeptide | 841-849 (D842V) |
| TSHR | Thyroid stimulating hormone receptor | 451-459 (M453T) |
| KIT | V-kit Hardy-Zuckerman 4 feline sarcoma viral oncogene homolog | 636-644 (K642E) |
| STAT3 | Signal transducer and activator of transcription 3 | a) 654-662 |
|  |  | b) 659-667 (D661Y) |
| CTNNB1 | Catenin (cadherin-associated protein), beta 1 | 30-39 (S33C) |
|  |  | 30-39 (S33F) |
|  |  | 30-39 (S33Y) |
| STK11 | Serine/threonine kinase 11 | 219-228 (P221L) |
| ERBB2 | V-erb-b2 erythroblastic leukemia viral oncogene homolog 2 | 773-782 (G776V) |
| SLIT2 | Slit homolog 2 | 8-16 (M8I) |
| CDKN2A | Cyclin-dependent kinase inhibitor 2A | 113-121 (P114L) |
| XPO1 | Exportin 1 | 568-576 (E571K) |

The above described TCR of the invention pertain in preferred embodiments to the following TCR molecules:

The present invention pertains to a TCR alpha chain, comprising a CDR3 region with the sequence shown in any one of SEQ ID NO: 28, 30, 32, 33, 36, 38 or 40. Preferred are TCR alpha chains comprising a variable domain having the sequence shown in any one of SEQ ID NO 42, 44, 46, 47, 50, 52, or 54.

The present invention pertains to a TCR beta chain, comprising a CDR3 region with the sequence shown in any one of SEQ ID NO: 29, 31, 34, 35, 37, 39 or 41. Preferred are TCR beta chains comprising a variable domain having the sequence shown in any one of SEQ ID NO 43, 45, 48, 49, 51, 53, or 55.

Preferred embodiments of the invention pertain to specific TCR isolated, or produced (obtained) according to any one of the methods as described herein. Such TCRs of the invention are preferably TCRs specific for targeting a mutated antigen selected from table 1 or 2. The Rac-1 or TRRAP mutated antigen are preferred. More specifically such TCRs are preferred which have the capacity to specifically bind to the mutated Rac-1 epitope FSGEYIPTV (SEQ ID NO:1), or the mutated TRAPP epitope KLVFGS-VFL SEQ ID NO:56).

Preferred TCR of the present invention are furthermore characterized by the presence of a CDR3 region comprising any one of the amino acid sequences shown in SEQ ID NO. 28 to 41. A Rac-1 TCR in accordance with the invention, with an alpha or beta chain, preferably comprises a CDR3 having a sequence shown in any one of SEQ ID NO: 28 to 39. A preferred TRRAP TCR in accordance with the present invention is characterized by the presence of a CDR3 amino acid sequence selected from the sequence shown in SEQ ID NO: 40 or 41.

More preferred is an alpha/beta TCR having an alpha chain comprising the CDR3 sequence shown in SEQ ID NO: 28, and a beta chain comprising the CDR3 sequence shown in SEQ ID NO: 29; an alpha/beta TCR having an alpha chain comprising the CDR3 sequence shown in SEQ ID NO: 30, and a beta chain comprising the CDR3 sequence shown in SEQ ID NO: 31; an alpha/beta TCR having an alpha chain comprising the CDR3 sequence shown in SEQ ID NO: 32, and a beta chain comprising the CDR3 sequence shown in SEQ ID NO: 34; an alpha/beta TCR having an alpha chain comprising the CDR3 sequence shown in SEQ ID NO: 32, and a beta chain comprising the CDR3 sequence shown in SEQ ID NO: 35; an alpha/beta TCR having an alpha chain comprising the CDR3 sequence shown in SEQ ID NO: 33, and a beta chain comprising the CDR3 sequence shown in SEQ ID NO: 34; an alpha/beta TCR having an alpha chain comprising the CDR3 sequence shown in SEQ ID NO: 33, and a beta chain comprising the CDR3 sequence shown in SEQ ID NO: 35; an alpha/beta TCR having an alpha chain comprising the CDR3 sequence shown in SEQ ID NO: 36, and a beta chain comprising the CDR3 sequence shown in SEQ ID NO: 37; an alpha/beta TCR having an alpha chain comprising the CDR3 sequence shown in SEQ ID NO: 38, and a beta chain comprising the CDR3 sequence shown in SEQ ID NO: 39; an alpha/beta TCR having an alpha chain comprising the CDR3 sequence shown in SEQ ID NO: 40, and a beta chain comprising the CDR3 sequence shown in SEQ ID NO: 41.

The TCR chains comprised in a TCR of the invention may furthermore comprise at least one, preferably two, most preferably all three CDR regions as present in one of the variable regions of any one of TCR 1 to 7. The sequences of said variable regions which contain all three CDR regions are shown in SEQ ID NO 42 to 55.

In another preferred embodiment the TCR of the invention comprises at least one variable region of an alpha and/or beta chain selected from a variable region of an alpha or beta chain of any one of the TCR T1 to T7 of the invention as depicted herein below in table 3.

The TCR as isolated in context of the present invention comprise the following variable regions (CDR3 regions are underlined):

```
Rac-1 TCR:
TRAV20*02-CAVQTSQGGSEKLVF-TRAJ57*01
                                        (SEQ ID NO: 42)
MEKMLECAFIV LWLQLGWLSG EDQVTQSPEA LRLQEGESSS

LNCSYTVSGL RGLFWYRQDP GKGPEFLFTL YSAGEEKEKE

RLKATLTKKE SFLHITAPKP EDSATYLCAV QTSQGGSEKL

VFGKGTKLTV NPYIQNPEPA

TRBV4-1*01-CASSQDASGIYYEQYF-TRBD2*02-
TRBJ2-7*01
                                        (SEQ ID NO: 43)
MGCRLLCCAV LCLLGAVPID TEVTQTPKHL VMGMTNKKSL

KCEQHMGHRA MYWYKQKAKK PPELMFVYSY EKLSINESVP

SRFSPECPNS SLLNLHLHAL QPEDSALYLC ASSQDASGIY

YEQYFGPGTR LTVT

TRAV13-1*01-CAASRGGAQKLVF-TRAJ54*01
                                        (SEQ ID NO: 44)
MTSIRAVFIF LWLQLDLVNG ENVEQHPSTL SVQEGDSAVI

KCTYSDSASN YFPWYKQELG KGPQLIIDIR SNVGEKKDQR

IAVTLNKTAK HFSLHITETQ PEDSAVYFCA ASRGGAQKLV

FGQGTRLTIN PN

TRBV3-1*01-CASSQLAGGPLYNEQFF-TRBD2*02-
TRBJ2-1*01
                                        (SEQ ID NO: 45)
MGCRLLCCVV FCLLQAGPLD TAVSQTPKYL VTQMGNDKSI

KCEQNLGHDT MYWYKQDSKK FLKIMFSYNN KELIINETVP

NRFSPKSPDK AHLNLHINSL ELGDSAVYFC ASSQLAGGPL

YNEQFFGPGT_RLTVL

TRAV5*01-CAESKRFSDGQKLLF-TRAJ16*01
                                        (SEQ ID NO: 46)
MR QVARVIVFLT LSMSRGEDVE QSLFLSVREG

DSSVINCTYT DSSSTYLYWY KQEPGAGLQL LTYIFSNMDM

KQDQRLTVLL NKKDKHLSLR IADTQTGDSA IYFCAESKRF

SDGQKLLFAR GTMLKVDLN

TRAV12-2*02-CAAQSARQLTF-TRAJ22*01
                                        (SEQ ID NO: 47)
M MKSLRVLLVI LWLQLSWVWS QQKEVEQNSG PLSVPEGAIA

SLNCTYSDRG SQSFFWYRQY SGKSPELIM SIYSNGDKED

GRFTAQLNKA SQYVSLLIRD SQPSDSATYL CAAQSARQLT

FGSGTQLTVL PD

TRBV20-1*01(/02)-CSARDLITDTQYF-TRBJ2-3*01
                                        (SEQ ID NO: 48)
MLLLLL LLGPGSGLGA VVSQHPSWVI CKSGTSVKIE

CRSLDFQATT MFWYRQFPKQ SLMLMATSNE GSKATYEQGV

EKDKFLINHA SLTLSTLTVT SAHPEDSSFY ICSARDLITD

TQYFGPGTRL TVL

TRBV3-1*01-CASSPWQETQYF-TRBJ2-5*01
                                        (SEQ ID NO: 49)
MGCRLL CCVVFCLLQA GPLDTAVSQT PKYLVTQMGN

DKSIKCEQNL GHDTMYWYKQ DSKKFLKIMF SYNNKELIIN

ETVPNRFSPK SPDKAHLNLH INSLELGDSA VYFCASSPWQ

ETQYFGPGTR LLVL

TRAV13-1*01 CAASLGSGNTPLVF TRAJ29*01
                                        (SEQ ID NO: 50)
M TSIRAVFIFL WLQLDLVNGE NVEQHPSTLS VQEGDSAVIK

CTYSDSASNY FPWYKQELGK GPQLIIDIRS NVGEKKDQRI

AVTLNKTAKH FSLHITETQP EDSAVYFCAA SLGSGNTPLV

FGKGTRLSVI AN

TRBV28*01 CASSLHSGRDTQYF TRBJ2-3*01 TRBD2*02
                                        (SEQ ID NO: 51)
MGIRLLCR VAFCFLAVGL VDVKVTQSSR YLVKRTGEKV

FLECVQDMDH ENMFWYRQDP GLGLRLIYFS YDVKMKEKGD

IPEGYSVSRE KKERFSLILE SASTNQTSMY LCASSLHSGR

DTQYFGPGTR LTVL
```

-continued

TRAV13-2*01 CAENRGANSKLTF TRAJ56*01 F
(SEQ ID NO: 52)
MMAGIRALF MYLWLQLDWV SRGESVGLHL PTLSVQEGDN

SIINCAYSNS ASDYFIWYKQ ESGKGPQFII DIRSNMDKRQ

GQRVTVLLNK TVKHLSLQIA ATQPGDSAVY F<u>CAENRGANS</u>

<u>KLTF</u>GKGITL SVRPD

TRBV12-3*01 CASSFTGGFYGYTF TRBJ1-2*01 TRBD1*01
(SEQ ID NO: 53)
MDSWTFCCVS LCILVAKHTD AGVIQSPRHE VTEMGQEVTL

RCKPISGHNS LFWYRQTMMR GLELLIYFNN NVPIDDSGMP

EDRFSAKMPN ASFSTLKIQP SEPRDSAVYF <u>CASSFTGGFY</u>

<u>GYTF</u>GSGTRL TVV

TRRAP TCR:
TRAV17*01-CATDWYTGANSKLTF-TRAJ56*01
(SEQ ID NO: 54)
METLLGVSLV ILWLQLARVN SQQGEEDPQA LSIQEGENAT

MNCSYKTSIN NLQWYRQNSG RGLVHLILIR SNEREKHSGR

LRVTLDTSKK SSSLLITASR AADTASYF<u>CA TDWYTGANSK</u>

<u>LTF</u>GKGITLS VRPD

TRBV6-2*01-CASSYSGYEQYF-TRBD1*01-TRBJ2-7*01
(SEQ ID NO: 55)
MSLGLLCCAA FSLLWAGPVN AGVTQTPKFR VLKTGQSMTL

LCAQDMNHEY MYWYRQDPGM GLRLIHYSVG EGTTAKGEVP

DGYNVSRLKK QNFLLGLESA APSQTSVYF<u>C ASSYSGYEQY</u>

<u>F</u>GPGTRLTVT

One further preferred embodiment of the invention provides a TCR alpha and/or beta chain, or a fragment thereof, comprising a sequence selected from the group of SEQ ID NO 42 to 55. Preferably the TCR of the invention is heterodimeric TCR comprising an alpha chain comprising a sequence according to SEQ ID NO 42, and a beta chain comprising a sequence according to SEQ ID NO 43, or comprising an alpha chain comprising a sequence according to SEQ ID NO 44, and a beta chain comprising a sequence according to SEQ ID NO 45, or comprising an alpha chain comprising a sequence according to SEQ ID NO 46, and a beta chain comprising a sequence according to SEQ ID NO 48, or comprising an alpha chain comprising a sequence according to SEQ ID NO 46, and a beta chain comprising a sequence according to SEQ ID NO 49, or comprising an alpha chain comprising a sequence according to SEQ ID NO 47, and a beta chain comprising a sequence according to SEQ ID NO 48, or comprising an alpha chain comprising a sequence according to SEQ ID NO 47, and a beta chain comprising a sequence according to SEQ ID NO 49, or comprising an alpha chain comprising a sequence according to SEQ ID NO 50, and a beta chain comprising a sequence according to SEQ ID NO 51, or comprising an alpha chain comprising a sequence according to SEQ ID NO 52, and a beta chain comprising a sequence according to SEQ ID NO 53, or comprising an alpha chain comprising a sequence according to SEQ ID NO 54, and a beta chain comprising a sequence according to SEQ ID NO 55.

In even more preferred aspects of the invention the TCR of the invention is a TCR comprising at least one TCR alpha or beta chain selected from the TCR chains of any one of TCRs T1 to T7 in table 3 below. Most preferred is that the TCR of the invention is an alpha/beta TCR selected from any one of T1 to T7 as depicted in table 3 herein below.

The aforementioned TCRs of the invention may in some embodiments contain altered amino acid sequences. Preferred is that TCR chains are encompassed by the present invention which are at least 70, 80, 90, 95, 96, 97, 98, or 99% identical to a TCR sequence, or TCR alpha or beta chain sequence, a TCR variable region according to any one of SEQ ID NO: 42 to 55, or a CDR3 sequence as disclosed herein. Most preferably a TCR of the invention comprises an alpha and/or beta chain which is at least 90%, or 95%, or 99% identical to an alpha/beta chain of any one of TCRs T1 to T7 as depicted in table 3.

The above described TCR are preferably specific for the mutated antigens of Rac-1 or TRRAP as disclosed in table 1 or 2, in particular when presented on a cell, such as a tumor cell or antigen presenting cell. Furthermore comprised by the present invention are functional fragments of the TCR or TCR chains of the invention. The term "functional fragment of the TCR or TCR chain" shall refer to a fragment of the full length receptor molecule, characterized in that the fragment is derived from that molecule and has maintained the same capability to bind the mutated TAA.

In a further aspect, as already disclosed above, the invention also pertains to the nucleic acids encoding for the TCR molecules of the invention as well as cells comprising these nucleic acids, or cells expressing said TCRs of the invention. The invention furthermore pertains to the use of the TCR proteins or nucleic acids, or cells, in the various methods or uses described herein before.

Preferably aspects of the invention relate to the treatment of tumorous diseases with the methods and various materials of the invention. Preferred diseases are cancers which are characterized by the expression of any one of the mutated TAA as disclosed herein. Preferred is a disease that is characterized by the expression of the mutated epitope of Rac-1 or TRRAP. Preferred diseases treated with a TCR of the invention that is specific for the Rac-1 mutated antigen or the TRRAP mutated antigen are selected from cancerous proliferative diseases, e.g. lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer. Particular preferred diseases for Rac1 specific TCRs are melanoma and non-small cell lung cancer.

The present invention will now be further described in the following examples with reference to the accompanying FIGURES and sequences, nevertheless, without being limited thereto. For the purposes of the present invention, all references as cited herein are incorporated by reference in their entireties. In the Figures and Sequences:

FIG. 1: shows the specific CD8+ T cell response against HLA-A201 restricted mutated RAC1P29S epitope in ABab-DII mice.

SEQ ID No 1 to 27: show mutated epitope sequences of HLA type A2 restricted TSAs as depicted in Table 1.

SEQ ID No 28 to 41: show the CDR3 domain sequences of the TCR of the invention.

SEQ ID No 42 to 55: show the variable regions of the TCR 1 to 7 of the invention.

EXAMPLES

Exemplary tumor specific antigen epitopes which are usable and preferred in the context of the present invention are provided in table 2.

| Gene | Protein | HLA A2.01 Epitope* | (SEQ ID NO.) |
|---|---|---|---|
| MELANOMA | | | |
| RAC1: | Ras-related C3 botulinum toxin substrate 1 | FP/SGEYIPTV | FPGEYIPTV (57)<br>FSGEYIPTV (1) |
| RAC2: | Ras-related C3 botulinum toxin substrate 1 | FP/LGEYIPTV | FPGEYIPTV (57)<br>FLGEYIPTV (2) |
| RHOT1: | Mitochondrial Rho GTPase 1 | FP/LEEVPPRA | FPEEVPPRA (58)<br>FLEEVPPRA (3) |
| MAP2K1: | Dual specificity mitogen-activated protein kinase1 | E/KIKLCDFGV | EIKLCDFGV (59)<br>KIKLCDFGV (4) |
| MAP2K2: | Dual specificity mitogen-activated protein kinase2 | E/KIKLCDFGV | EIKLCDFGV (59)<br>KIKLCDFGV (5) |
| | | S/FLDQVLKEA | SLDQVLKEA (60)<br>FLDQVLKEA (6) |
| Nos1: | Nitric oxide synthase | KS/LQAYAKTL | KSQAYAKTL (61)<br>KLQAYAKTL (7) |
| LUNG TUMOR | | | |
| EGFR: | Epidermal growth factor receptor | VLG/ASGAFGT | VLGSGAFGT (62)<br>VLASGAFGT (8) |
| SMCA4: | Transcription activator BRG1 | LLSTRAG/WGL | LLSTRAGGL (63)<br>LLSTRAWGL (9) |
| STK11: | Serine/threonine-protein kinas | FQP/LPEIANGL | FQPPEIANGL (64)<br>FQLPEIANGL (10) |
| ARID1A: | AT-rich interactive domain-containing protein 1A | MW/LVDRYLAFT | MWVDRYLAFT (65)<br>MLVDRYLAFT (11) |
| | | FE/VMSKHPGL | FEMSKHPGL (66)<br>FVMSKHPGL (12) |
| RBM10: | RNA-binding protein 10 | I/FLGALAPYA | ILGALAPYA (67)<br>FLGALAPYA (13) |
| U2AF1: | Splicing factor U2AF 26 kDa subunit | RHGDRCS/FRL | RHGDRCSRL (68)<br>RHGDRCFRL (14) |
| ENDOMETRIAL TUMORS | | | |
| EP300: | Histone acetyltransferase p300 | LMDGR/WDAFL | LMDGRDAFL (69)<br>LMDGWDAFL (15) |
| | | LMDGR/QDAFL | LMDGRDAFL (69)<br>LMDGQDAFL (16) |
| CHD4 | Chromodomain-helicase-DNA-binding protein 4 | NLEEL/VFHLL | NLEELFHLL (70)<br>NLEEVFHLL (17) |
| FBXW7: | F-box/WD repeat-containing protein 7 | TLYGHTF/SAV | TLYGHTFAV (71)<br>TLYGHTSAV (18) |
| | | TLYGHTFA/TV | TLYGHTFAV (71)<br>TLYGHTFTV (19) |
| GLIOMA | | | |
| H3F3A: | Histone H3.3 | QLATKAARK/M | QLATKAARK (72)<br>QLATKAARM (20) |
| | | KSAPSTG/VGV | KSAPSTGGV (73)<br>KSAPSTVGV (21) |
| CLL | | | |
| KLHL6: | Kelch-like protein 6 | KF/LDDAGLSL | KFDDAGLSL (74)<br>KLDDAGLSL (22) |
| PROSTATE TUMOR | | | |
| SPOP: | Speckle-type POZ protein | YLSLY/NLLLV | YLSLYLLLV (75)<br>YLSLNLLLV (23) |
| | | YLSLY/CLLLV | YLSLYLLLV (75)<br>YLSLCLLLV (24) |
| | | FVQGKDWGF/V | FVQGKDWGF (76)<br>FVQGKDWGV (25) |
| | | FVQGKDWGF/L | FVQGKDWGF (76)<br>FVQGKDWGL (26) |
| MED12: | Mediator of RNA polymerase II transcription subunit 12 | VLYD/EQPRHV | VLYDQPRHV (77)<br>VLYEQPRHV (27) |

*wildtype/mutated amino acid

Example 1

RAC1 Specific TCR Against the FSGEYIPTV Epitope

For the generation of T-cells bearing a RAC1 TSA specific TCR, mice deficient in their endogenous TCR loci and expressing the human TCR repertoire were used. The production and setup of the transgenic mice (ABabDII mice) are in detail described elsewhere (Li L P, Lampert J C, Chen X, Leitao C, Popovic J, Muller W, et al. Transgenic mice with a diverse human T cell antigen receptor repertoire. Nat Med. 2010; 16:1029-34.).

ABabDII mice were immunized twice with mutated RAC1P29S epitope (see above). Seven days after the last immunization, pooled spleen and lymph node cells were stimulated in vitro with RAC1 mutant or wildtype peptides and analyzed for expression of CD3, CD8 and intracellular IFN-γ. FIG. 1 shows CD8+ and IFN-γ+ cells within the CD3+ cell population (percentages indicated by numbers). In parentheses, the percentage of CD8+ and IFN-γ+ T cells within the CD8+ T cell population is given.

Example 2

RAC1 and TRRAP Specific TCR of the Invention

TABLE 3

| | | | The following TCR could be isolated: | |
|---|---|---|---|---|
| TCR | Antigen | peptide/purification | TCR sequence | CDR3* |
| T1 | Rac-1 | FSGEYIPTV | TRAV20*02-CAVQTSQGGSEKLVF-TRAJ57*01 | 28 |
| | | IFNg-CAPTURE | TRBV4-1*01-CASSQDASGIYYEQYF-TRBD2*02-TRBJ2-7*01 | 29 |
| T2 | Rac-1 | FSGEYIPTV | TRAV13-1*01-CAASRGGAQKLVF-TRAJ54*01 | 30 |
| | | IFNg-CAPTURE | TRBV3-1*01-CASSQLAGGPLYNEQFF-TRBD2*02-TRBJ2-1*01 | 31 |
| T3/T4 | Rac-1 | FSGEYIPTV | TRAV5*01-CAESKRFSDGQKLLF-TRAJ16*01 | 32 |
| | | A2-TETRAMER | TRAV12-2*02-CAAQSARQLTF-TRAJ22*01 | 33 |
| | | | TRBV20-1*01(/02)-CSARDLITDTQYF-TRBJ2-3*01 | 34 |
| | | | TRBV3-1*01-CASSPWQETQYF-TRBJ2-5*01 | 35 |
| T5 | Rac-1 | FSGEYIPTV | TRAV13-1*01 CAASLGSGNTPLVF TRAJ29*01 | 36 |
| | | A2-TETRAMER | TRBV28*01 CASSLHSGRDTQYF TRBJ2-3*01 TRBD2*02 | 37 |
| T6 | Rac-1 | FSGEYIPTV | TRAV13-2*01 CAENRGANSKLTF TRAJ56*01 F | 38 |
| | | A2-TETRAMER | TRBV12-3*01 CASSFTGGFYGYTF TRBJ1-2*01 TRBD1*01 | 39 |
| T7 | TRRAP | KLVFGSVFL | TRAV17*01-CATDWYTGANSKLTF-TRAJ56*01 | 40 |
| | | IFNg-CAPTURE | TRBV6-2*01-CASSYSGYEQYF-TRBD1*01-TRBJ2-7*01 | 41 |

*Sequence identifier

Table 3 provides the sequences of the alpha and beta chains of the isolated TCR of the invention (T1 to T7). The sequences are presented by the known TCR allele sequence and the specific CDR3 amino acid sequence of the TCR of the invention. TCR allele nomenclature is derived from the TCR allele Database IMGT (http://www.imgt.org/vquest/refseqh.html#VQUEST) Lefranc, M.-P. and Lefranc, G. The T cell receptor FactsBook Academic Press, London, UK (398 pages), (2001).

The variable regions of the TCR chains of the TCR 1 to 7 are provided in SEQ ID No 42 to 55.

For T3/T4, the inventors discovered that in particular the chain combination TRAV5/TRBV20-1 (SEQ ID NO: 32 and 34) shows good binding to the Rac1-tetramer.

The invention claimed is:

1. A protein which is a T-cell receptor comprising an alpha chain and a beta chain, wherein
   (i) the alpha chain comprises all three complementarity determining regions (CDRs) present in SEQ ID NO: 42, and said beta chain comprises all three CDRs present in SEQ ID NO: 43; or
   (ii) the alpha chain comprises all three complementarity determining regions (CDRs) present in SEQ ID NO: 44, and said beta chain comprises all three CDRs present in SEQ ID NO: 45; or
   (iii) the alpha chain comprises all three complementarity determining regions (CDRs) present in SEQ ID NO: 46, and said beta chain comprises all three CDRs present in SEQ ID NO: 48; or
   (iv) the alpha chain comprises all three complementarity determining regions (CDRs) present in SEQ ID: 47, and said beta chain comprises all three CDRs present in SEQ ID NO: 49; or
   (v) the alpha chain comprises all three complementarity determining regions (CDRs) present in SEQ ID NO: 50, and said beta chain comprises all three CDRs present in SEQ ID NO: 51: or
   (vi) the alpha chain comprises all three complementarity determining regions (CDRs) present in SEQ ID NO: 52, and said beta chain comprises all three CDRs present in SEQ ID NO: 53.

2. The protein according to claim 1, which is an alpha/beta single chain TCR (scTCR).

3. The protein according to claim 1, which is fused to a human cytokine.

4. The protein according to claim 1, which is fused to IL-2, IL7 or IL-15.

* * * * *

```
                        SEQUENCE LISTING

<160> NUMBER OF SEQ ID NOS: 77

<210> SEQ ID NO 1
<211> LENGTH: 9
<212> TYPE: PRT
<213> ORGANISM: Homo sapiens

<400> SEQUENCE: 1

Phe Ser Gly Glu Tyr Ile Pro Thr Val
1               5

<210> SEQ ID NO 2
<211> LENGTH: 9
<212> TYPE: PRT
<213> ORGANISM: Homo sapiens

<400> SEQUENCE: 2

Phe Leu Gly Glu Tyr Ile Pro Thr Val
1               5

<210> SEQ ID NO 3
<211> LENGTH: 9
<212> TYPE: PRT
<213> ORGANISM: Homo sapiens

<400> SEQUENCE: 3

Phe Leu Glu Glu Val Pro Pro Arg Ala
1               5

<210> SEQ ID NO 4
<211> LENGTH: 9
<212> TYPE: PRT
<213> ORGANISM: Homo sapiens

<400> SEQUENCE: 4

Lys Ile Lys Leu Cys Asp Phe Gly Val
1               5

<210> SEQ ID NO 5
<211> LENGTH: 9
<212> TYPE: PRT
<213> ORGANISM: Homo sapiens

<400> SEQUENCE: 5

Lys Ile Lys Leu Cys Asp Phe Gly Val
1               5

<210> SEQ ID NO 6
<211> LENGTH: 9
<212> TYPE: PRT
<213> ORGANISM: Homo sapiens

<400> SEQUENCE: 6

Phe Leu Asp Gln Val Leu Lys Glu Ala
1               5
```

```
<210> SEQ ID NO 7
<211> LENGTH: 9
<212> TYPE: PRT
<213> ORGANISM: Homo sapiens

<400> SEQUENCE: 7

Lys Leu Gln Ala Tyr Ala Lys Thr Leu
1               5

<210> SEQ ID NO 8
<211> LENGTH: 9
<212> TYPE: PRT
<213> ORGANISM: Homo sapiens

<400> SEQUENCE: 8

Val Leu Ala Ser Gly Ala Phe Gly Thr
1               5

<210> SEQ ID NO 9
<211> LENGTH: 9
<212> TYPE: PRT
<213> ORGANISM: Homo sapiens

<400> SEQUENCE: 9

Leu Leu Ser Thr Arg Ala Trp Gly Leu
1               5

<210> SEQ ID NO 10
<211> LENGTH: 10
<212> TYPE: PRT
<213> ORGANISM: Homo sapiens

<400> SEQUENCE: 10

Phe Gln Leu Pro Glu Ile Ala Asn Gly Leu
1               5                   10

<210> SEQ ID NO 11
<211> LENGTH: 10
<212> TYPE: PRT
<213> ORGANISM: Homo sapiens

<400> SEQUENCE: 11

Met Leu Val Asp Arg Tyr Leu Ala Phe Thr
1               5                   10

<210> SEQ ID NO 12
<211> LENGTH: 9
<212> TYPE: PRT
<213> ORGANISM: Homo sapiens

<400> SEQUENCE: 12

Phe Val Met Ser Lys His Pro Gly Leu
1               5

<210> SEQ ID NO 13
<211> LENGTH: 9
<212> TYPE: PRT
<213> ORGANISM: Homo sapiens

<400> SEQUENCE: 13

Phe Leu Gly Ala Leu Ala Pro Tyr Ala
1               5
```

```
<210> SEQ ID NO 14
<211> LENGTH: 9
<212> TYPE: PRT
<213> ORGANISM: Homo sapiens

<400> SEQUENCE: 14

Arg His Gly Asp Arg Cys Phe Arg Leu
1               5

<210> SEQ ID NO 15
<211> LENGTH: 9
<212> TYPE: PRT
<213> ORGANISM: Homo sapiens

<400> SEQUENCE: 15

Leu Met Asp Gly Trp Asp Ala Phe Leu
1               5

<210> SEQ ID NO 16
<211> LENGTH: 9
<212> TYPE: PRT
<213> ORGANISM: Homo sapiens

<400> SEQUENCE: 16

Leu Met Asp Gly Gln Asp Ala Phe Leu
1               5

<210> SEQ ID NO 17
<211> LENGTH: 9
<212> TYPE: PRT
<213> ORGANISM: Homo sapiens

<400> SEQUENCE: 17

Asn Leu Glu Glu Val Phe His Leu Leu
1               5

<210> SEQ ID NO 18
<211> LENGTH: 9
<212> TYPE: PRT
<213> ORGANISM: Homo sapiens

<400> SEQUENCE: 18

Thr Leu Tyr Gly His Thr Ser Ala Val
1               5

<210> SEQ ID NO 19
<211> LENGTH: 9
<212> TYPE: PRT
<213> ORGANISM: Homo sapiens

<400> SEQUENCE: 19

Thr Leu Tyr Gly His Thr Phe Thr Val
1               5

<210> SEQ ID NO 20
<211> LENGTH: 9
<212> TYPE: PRT
<213> ORGANISM: Homo sapiens

<400> SEQUENCE: 20

Gln Leu Ala Thr Lys Ala Ala Arg Met
1               5

<210> SEQ ID NO 21
<211> LENGTH: 9
```

```
<212> TYPE: PRT
<213> ORGANISM: Homo sapiens

<400> SEQUENCE: 21

Lys Ser Ala Pro Ser Thr Val Gly Val
1               5

<210> SEQ ID NO 22
<211> LENGTH: 9
<212> TYPE: PRT
<213> ORGANISM: Homo sapiens

<400> SEQUENCE: 22

Lys Leu Asp Asp Ala Gly Leu Ser Leu
1               5

<210> SEQ ID NO 23
<211> LENGTH: 9
<212> TYPE: PRT
<213> ORGANISM: Homo sapiens

<400> SEQUENCE: 23

Tyr Leu Ser Leu Asn Leu Leu Leu Val
1               5

<210> SEQ ID NO 24
<211> LENGTH: 9
<212> TYPE: PRT
<213> ORGANISM: Homo sapiens

<400> SEQUENCE: 24

Tyr Leu Ser Leu Cys Leu Leu Leu Val
1               5

<210> SEQ ID NO 25
<211> LENGTH: 9
<212> TYPE: PRT
<213> ORGANISM: Homo sapiens

<400> SEQUENCE: 25

Phe Val Gln Gly Lys Asp Trp Gly Val
1               5

<210> SEQ ID NO 26
<211> LENGTH: 9
<212> TYPE: PRT
<213> ORGANISM: Homo sapiens

<400> SEQUENCE: 26

Phe Val Gln Gly Lys Asp Trp Gly Leu
1               5

<210> SEQ ID NO 27
<211> LENGTH: 9
<212> TYPE: PRT
<213> ORGANISM: Homo sapiens

<400> SEQUENCE: 27

Val Leu Tyr Glu Gln Pro Arg His Val
1               5

<210> SEQ ID NO 28
<211> LENGTH: 15
<212> TYPE: PRT
<213> ORGANISM: Homo sapiens
```

```
<400> SEQUENCE: 28

Cys Ala Val Gln Thr Ser Gln Gly Gly Ser Glu Lys Leu Val Phe
1               5                   10                  15

<210> SEQ ID NO 29
<211> LENGTH: 16
<212> TYPE: PRT
<213> ORGANISM: Homo sapiens

<400> SEQUENCE: 29

Cys Ala Ser Ser Gln Asp Ala Ser Gly Ile Tyr Tyr Glu Gln Tyr Phe
1               5                   10                  15

<210> SEQ ID NO 30
<211> LENGTH: 13
<212> TYPE: PRT
<213> ORGANISM: Homo sapiens

<400> SEQUENCE: 30

Cys Ala Ala Ser Arg Gly Gly Ala Gln Lys Leu Val Phe
1               5                   10

<210> SEQ ID NO 31
<211> LENGTH: 17
<212> TYPE: PRT
<213> ORGANISM: Homo sapiens

<400> SEQUENCE: 31

Cys Ala Ser Ser Gln Leu Ala Gly Gly Pro Leu Tyr Asn Glu Gln Phe
1               5                   10                  15

Phe

<210> SEQ ID NO 32
<211> LENGTH: 15
<212> TYPE: PRT
<213> ORGANISM: Homo sapiens

<400> SEQUENCE: 32

Cys Ala Glu Ser Lys Arg Phe Ser Asp Gly Lys Leu Leu Phe
1               5                   10                  15

<210> SEQ ID NO 33
<211> LENGTH: 11
<212> TYPE: PRT
<213> ORGANISM: Homo sapiens

<400> SEQUENCE: 33

Cys Ala Ala Gln Ser Ala Arg Gln Leu Thr Phe
1               5                   10

<210> SEQ ID NO 34
<211> LENGTH: 13
<212> TYPE: PRT
<213> ORGANISM: Homo sapiens

<400> SEQUENCE: 34

Cys Ser Ala Arg Asp Leu Ile Thr Asp Thr Gln Tyr Phe
1               5                   10

<210> SEQ ID NO 35
<211> LENGTH: 12
<212> TYPE: PRT
<213> ORGANISM: Homo sapiens
```

<400> SEQUENCE: 35

Cys Ala Ser Ser Pro Trp Gln Glu Thr Gln Tyr Phe
1               5                   10

<210> SEQ ID NO 36
<211> LENGTH: 14
<212> TYPE: PRT
<213> ORGANISM: Homo sapiens

<400> SEQUENCE: 36

Cys Ala Ala Ser Leu Gly Ser Gly Asn Thr Pro Leu Val Phe
1               5                   10

<210> SEQ ID NO 37
<211> LENGTH: 14
<212> TYPE: PRT
<213> ORGANISM: Homo sapiens

<400> SEQUENCE: 37

Cys Ala Ser Ser Leu His Ser Gly Arg Asp Thr Gln Tyr Phe
1               5                   10

<210> SEQ ID NO 38
<211> LENGTH: 13
<212> TYPE: PRT
<213> ORGANISM: Homo sapiens

<400> SEQUENCE: 38

Cys Ala Glu Asn Arg Gly Ala Asn Ser Lys Leu Thr Phe
1               5                   10

<210> SEQ ID NO 39
<211> LENGTH: 14
<212> TYPE: PRT
<213> ORGANISM: Homo sapiens

<400> SEQUENCE: 39

Cys Ala Ser Ser Phe Thr Gly Gly Phe Tyr Gly Tyr Thr Phe
1               5                   10

<210> SEQ ID NO 40
<211> LENGTH: 15
<212> TYPE: PRT
<213> ORGANISM: Homo sapiens

<400> SEQUENCE: 40

Cys Ala Thr Asp Trp Tyr Thr Gly Ala Asn Ser Lys Leu Thr Phe
1               5                   10                  15

<210> SEQ ID NO 41
<211> LENGTH: 12
<212> TYPE: PRT
<213> ORGANISM: Homo sapiens

<400> SEQUENCE: 41

Cys Ala Ser Ser Tyr Ser Gly Tyr Glu Gln Tyr Phe
1               5                   10

<210> SEQ ID NO 42
<211> LENGTH: 141
<212> TYPE: PRT
<213> ORGANISM: Homo sapiens

<400> SEQUENCE: 42

```
Met Glu Lys Met Leu Glu Cys Ala Phe Ile Val Leu Trp Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Leu Asn Cys Ser Tyr Thr Val
        35                  40                  45

Ser Gly Leu Arg Gly Leu Phe Trp Tyr Arg Gln Asp Pro Gly Lys Gly
50                  55                  60

Pro Glu Phe Leu Phe Thr Leu Tyr Ser Ala Gly Glu Glu Lys Glu Lys
65              70                  75                  80

Glu Arg Leu Lys Ala Thr Leu Thr Lys Lys Glu Ser Phe Leu His Ile
                85                  90                      95

Thr Ala Pro Lys Pro Glu Asp Ser Ala Thr Tyr Leu Cys Ala Val Gln
                100                 105                 110

Thr Ser Gln Gly Gly Ser Glu Lys Leu Val Phe Gly Lys Gly Thr Lys
            115                 120                 125

Leu Thr Val Asn Pro Tyr Ile Gln Asn Pro Glu Pro Ala
    130                 135                 140

<210> SEQ ID NO 43
<211> LENGTH: 134
<212> TYPE: PRT
<213> ORGANISM: Homo sapiens

<400> SEQUENCE: 43

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
50                  55                  60

Met Phe Val Tyr Ser Tyr Glu Lys Leu Ser Ile Asn Glu Ser Val Pro
65              70                  75                  80

Ser Arg Phe Ser Pro Glu Cys Pro Asn Ser Ser Leu Leu Asn Leu His
                85                  90                      95

Leu His Ala Leu Gln Pro Glu Asp Ser Ala Leu Tyr Leu Cys Ala Ser
                100                 105                 110

Ser Gln Asp Ala Ser Gly Ile Tyr Tyr Glu Gln Tyr Phe Gly Pro Gly
            115                 120                 125

Thr Arg Leu Thr Val Thr
    130

<210> SEQ ID NO 44
<211> LENGTH: 132
<212> TYPE: PRT
<213> ORGANISM: Homo sapiens

<400> SEQUENCE: 44

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45
```

```
Ser Asn Tyr Phe Pro Trp Tyr Lys Gln Glu Leu Gly Lys Gly Pro Gln
 50                  55                  60

Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

Thr Glu Thr Gln Pro Glu Asp Ser Ala Val Tyr Phe Cys Ala Ala Ser
                100                 105                 110

Arg Gly Gly Ala Gln Lys Leu Val Phe Gly Gln Gly Thr Arg Leu Thr
                115                 120                 125

Ile Asn Pro Asn
            130

<210> SEQ ID NO 45
<211> LENGTH: 135
<212> TYPE: PRT
<213> ORGANISM: Homo sapiens

<400> SEQUENCE: 45

Met Gly Cys Arg Leu Leu Cys Cys Val Phe Cys Leu Leu Gln Ala
 1               5                  10                  15

Gly Pro Leu Asp Thr Ala Val Ser Gln Thr Pro Lys Tyr Leu Val Thr
                 20                  25                  30

Gln Met Gly Asn Asp Lys Ser Ile Lys Cys Glu Gln Asn Leu Gly His
                 35                  40                  45

Asp Thr Met Tyr Trp Tyr Lys Gln Asp Ser Lys Lys Phe Leu Lys Ile
 50                  55                  60

Met Phe Ser Tyr Asn Asn Lys Glu Leu Ile Ile Asn Glu Thr Val Pro
 65                  70                  75                  80

Asn Arg Phe Ser Pro Lys Ser Pro Asp Lys Ala His Leu Asn Leu His
                 85                  90                  95

Ile Asn Ser Leu Glu Leu Gly Asp Ser Ala Val Tyr Phe Cys Ala Ser
                100                 105                 110

Ser Gln Leu Ala Gly Gly Pro Leu Tyr Asn Glu Gln Phe Phe Gly Pro
                115                 120                 125

Gly Thr Arg Leu Thr Val Leu
            130                 135

<210> SEQ ID NO 46
<211> LENGTH: 131
<212> TYPE: PRT
<213> ORGANISM: Homo sapiens

<400> SEQUENCE: 46

Met Arg Gln Val Ala Arg Val Ile Val Phe Leu Thr Leu Ser Met Ser
 1               5                  10                  15

Arg Gly Glu Asp Val Glu Gln Ser Leu Phe Leu Ser Val Arg Glu Gly
                 20                  25                  30

Asp Ser Ser Val Ile Asn Cys Thr Tyr Thr Asp Ser Ser Ser Thr Tyr
                 35                  40                  45

Leu Tyr Trp Tyr Lys Gln Glu Pro Gly Ala Gly Leu Gln Leu Leu Thr
 50                  55                  60

Tyr Ile Phe Ser Asn Met Asp Met Lys Gln Asp Gln Arg Leu Thr Val
 65                  70                  75                  80

Leu Leu Asn Lys Lys Asp Lys His Leu Ser Leu Arg Ile Ala Asp Thr
                 85                  90                  95
```

```
Gln Thr Gly Asp Ser Ala Ile Tyr Phe Cys Ala Glu Ser Lys Arg Phe
            100                 105                 110

Ser Asp Gly Gln Lys Leu Leu Phe Ala Arg Gly Thr Met Leu Lys Val
        115                 120                 125

Asp Leu Asn
    130

<210> SEQ ID NO 47
<211> LENGTH: 132
<212> TYPE: PRT
<213> ORGANISM: Homo sapiens

<400> SEQUENCE: 47

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Ala Gln Ser Ala Arg Gln Leu Thr Phe Gly Ser Gly Thr Gln Leu Thr
        115                 120                 125

Val Leu Pro Asp
    130

<210> SEQ ID NO 48
<211> LENGTH: 129
<212> TYPE: PRT
<213> ORGANISM: Homo sapiens

<400> SEQUENCE: 48

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Asp
            100                 105                 110

Leu Ile Thr Asp Thr Gln Tyr Phe Gly Pro Gly Thr Arg Leu Thr Val
        115                 120                 125

Leu
```

```
<210> SEQ ID NO 49
<211> LENGTH: 130
<212> TYPE: PRT
<213> ORGANISM: Homo sapiens

<400> SEQUENCE: 49

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Pro Trp Gln Glu Thr Gln Tyr Phe Gly Pro Gly Thr Arg Leu Leu
        115                 120                 125

Val Leu
    130

<210> SEQ ID NO 50
<211> LENGTH: 133
<212> TYPE: PRT
<213> ORGANISM: Homo sapiens

<400> SEQUENCE: 50

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Leu Gly Ser Gly Asn Thr Pro Leu Val Phe Gly Lys Gly Thr Arg Leu
        115                 120                 125

Ser Val Ile Ala Asn
    130

<210> SEQ ID NO 51
<211> LENGTH: 132
<212> TYPE: PRT
<213> ORGANISM: Homo sapiens

<400> SEQUENCE: 51

Met Gly Ile Arg Leu Leu Cys Arg Val Ala Phe Cys Phe Leu Ala Val
```

```
                1               5                   10                  15
        Gly Leu Val Asp Val Lys Val Thr Gln Ser Ser Arg Tyr Leu Val Lys
                        20                  25                  30

Arg Thr Gly Glu Lys Val Phe Leu Glu Cys Val Gln Asp Met Asp His
                        35                  40                  45

Glu Asn Met Phe Trp Tyr Arg Gln Asp Pro Gly Leu Gly Leu Arg Leu
                        50                  55                  60

Ile Tyr Phe Ser Tyr Asp Val Lys Met Lys Glu Lys Gly Asp Ile Pro
        65                  70                  75                  80

Glu Gly Tyr Ser Val Ser Arg Glu Lys Lys Glu Arg Phe Ser Leu Ile
                        85                  90                  95

Leu Glu Ser Ala Ser Thr Asn Gln Thr Ser Met Tyr Leu Cys Ala Ser
                        100                 105                 110

Ser Leu His Ser Gly Arg Asp Thr Gln Tyr Phe Gly Pro Gly Thr Arg
                        115                 120                 125

Leu Thr Val Leu
                130

<210> SEQ ID NO 52
<211> LENGTH: 134
<212> TYPE: PRT
<213> ORGANISM: Homo sapiens

<400> SEQUENCE: 52

Met Met Ala Gly Ile Arg Ala Leu Phe Met Tyr Leu Trp Leu Gln Leu
1               5                   10                  15

Asp Trp Val Ser Arg Gly Glu Ser Val Gly Leu His Leu Pro Thr Leu
                20                  25                  30

Ser Val Gln Glu Gly Asp Asn Ser Ile Ile Asn Cys Ala Tyr Ser Asn
                35                  40                  45

Ser Ala Ser Asp Tyr Phe Ile Trp Tyr Lys Gln Glu Ser Gly Lys Gly
                50                  55                  60

Pro Gln Phe Ile Ile Asp Ile Arg Ser Asn Met Asp Lys Arg Gln Gly
65                  70                  75                  80

Gln Arg Val Thr Val Leu Leu Asn Lys Thr Val Lys His Leu Ser Leu
                85                  90                  95

Gln Ile Ala Ala Thr Gln Pro Gly Asp Ser Ala Val Tyr Phe Cys Ala
                100                 105                 110

Glu Asn Arg Gly Ala Asn Ser Lys Leu Thr Phe Gly Lys Gly Ile Thr
                115                 120                 125

Leu Ser Val Arg Pro Asp
                130

<210> SEQ ID NO 53
<211> LENGTH: 133
<212> TYPE: PRT
<213> ORGANISM: Homo sapiens

<400> SEQUENCE: 53

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
                35                  40                  45

Asn Ser Leu Phe Trp Tyr Arg Gln Thr Met Met Arg Gly Leu Glu Leu
```

```
                50                  55                  60
Leu Ile Tyr Phe Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                     85                  90                  95

Lys Ile Gln Pro Ser Glu Pro Arg Asp Ser Ala Val Tyr Phe Cys Ala
                100                 105                 110

Ser Ser Phe Thr Gly Gly Phe Tyr Gly Tyr Thr Phe Gly Ser Gly Thr
            115                 120                 125

Arg Leu Thr Val Val
        130

<210> SEQ ID NO 54
<211> LENGTH: 134
<212> TYPE: PRT
<213> ORGANISM: Homo sapiens

<400> SEQUENCE: 54

Met Glu Thr Leu Leu Gly Val Ser Leu Val Ile Leu Trp Leu Gln Leu
 1               5                  10                  15

Ala Arg Val Asn Ser Gln Gln Gly Glu Glu Asp Pro Gln Ala Leu Ser
                20                  25                  30

Ile Gln Glu Gly Glu Asn Ala Thr Met Asn Cys Ser Tyr Lys Thr Ser
            35                  40                  45

Ile Asn Asn Leu Gln Trp Tyr Arg Gln Asn Ser Gly Arg Gly Leu Val
 50                  55                  60

His Leu Ile Leu Ile Arg Ser Asn Glu Arg Glu Lys His Ser Gly Arg
 65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
                100                 105                 110

Trp Tyr Thr Gly Ala Asn Ser Lys Leu Thr Phe Gly Lys Gly Ile Thr
            115                 120                 125

Leu Ser Val Arg Pro Asp
        130

<210> SEQ ID NO 55
<211> LENGTH: 130
<212> TYPE: PRT
<213> ORGANISM: Homo sapiens

<400> SEQUENCE: 55

Met Ser Leu Gly Leu Leu Cys Cys Ala Ala Phe Ser Leu Leu Trp Ala
 1               5                  10                  15

Gly Pro Val Asn Ala Gly Val Thr Gln Thr Pro Lys Phe Arg Val Leu
                20                  25                  30

Lys Thr Gly Gln Ser Met Thr Leu Leu Cys Ala Gln Asp Met Asn His
                 35                  40                  45

Glu Tyr Met Tyr Trp Tyr Arg Gln Asp Pro Gly Met Gly Leu Arg Leu
 50                  55                  60

Ile His Tyr Ser Val Gly Glu Gly Thr Thr Ala Lys Gly Glu Val Pro
 65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
```

-continued

```
            100                 105                 110

Ser Tyr Ser Gly Tyr Glu Gln Tyr Phe Gly Pro Gly Thr Arg Leu Thr
        115                 120                 125

Val Thr
    130

<210> SEQ ID NO 56
<211> LENGTH: 9
<212> TYPE: PRT
<213> ORGANISM: Artificial
<220> FEATURE:
<223> OTHER INFORMATION: mutated TRAPP epitope

<400> SEQUENCE: 56

Lys Leu Val Phe Gly Ser Val Phe Leu
1               5

<210> SEQ ID NO 57
<211> LENGTH: 9
<212> TYPE: PRT
<213> ORGANISM: Homo sapiens

<400> SEQUENCE: 57

Phe Pro Gly Glu Tyr Ile Pro Thr Val
1               5

<210> SEQ ID NO 58
<211> LENGTH: 9
<212> TYPE: PRT
<213> ORGANISM: Homo sapiens

<400> SEQUENCE: 58

Phe Pro Glu Glu Val Pro Pro Arg Ala
1               5

<210> SEQ ID NO 59
<211> LENGTH: 9
<212> TYPE: PRT
<213> ORGANISM: Homo sapiens

<400> SEQUENCE: 59

Glu Ile Lys Leu Cys Asp Phe Gly Val
1               5

<210> SEQ ID NO 60
<211> LENGTH: 9
<212> TYPE: PRT
<213> ORGANISM: Homo sapiens

<400> SEQUENCE: 60

Ser Leu Asp Gln Val Leu Lys Glu Ala
1               5

<210> SEQ ID NO 61
<211> LENGTH: 9
<212> TYPE: PRT
<213> ORGANISM: Homo sapiens

<400> SEQUENCE: 61

Lys Ser Gln Ala Tyr Ala Lys Thr Leu
1               5

<210> SEQ ID NO 62
<211> LENGTH: 9
```

<212> TYPE: PRT
<213> ORGANISM: Homo sapiens

<400> SEQUENCE: 62

Val Leu Gly Ser Gly Ala Phe Gly Thr
1               5

<210> SEQ ID NO 63
<211> LENGTH: 9
<212> TYPE: PRT
<213> ORGANISM: Homo sapiens

<400> SEQUENCE: 63

Leu Leu Ser Thr Arg Ala Gly Gly Leu
1               5

<210> SEQ ID NO 64
<211> LENGTH: 10
<212> TYPE: PRT
<213> ORGANISM: Homo sapiens

<400> SEQUENCE: 64

Phe Gln Pro Pro Glu Ile Ala Asn Gly Leu
1               5                   10

<210> SEQ ID NO 65
<211> LENGTH: 10
<212> TYPE: PRT
<213> ORGANISM: Homo sapiens

<400> SEQUENCE: 65

Met Trp Val Asp Arg Tyr Leu Ala Phe Thr
1               5                   10

<210> SEQ ID NO 66
<211> LENGTH: 9
<212> TYPE: PRT
<213> ORGANISM: Homo sapiens

<400> SEQUENCE: 66

Phe Glu Met Ser Lys His Pro Gly Leu
1               5

<210> SEQ ID NO 67
<211> LENGTH: 9
<212> TYPE: PRT
<213> ORGANISM: Homo sapiens

<400> SEQUENCE: 67

Ile Leu Gly Ala Leu Ala Pro Tyr Ala
1               5

<210> SEQ ID NO 68
<211> LENGTH: 9
<212> TYPE: PRT
<213> ORGANISM: Homo sapiens

<400> SEQUENCE: 68

Arg His Gly Asp Arg Cys Ser Arg Leu
1               5

<210> SEQ ID NO 69
<211> LENGTH: 9
<212> TYPE: PRT
<213> ORGANISM: Homo sapiens

<400> SEQUENCE: 69

Leu Met Asp Gly Arg Asp Ala Phe Leu
1               5

<210> SEQ ID NO 70
<211> LENGTH: 9
<212> TYPE: PRT
<213> ORGANISM: Homo sapiens

<400> SEQUENCE: 70

Asn Leu Glu Glu Leu Phe His Leu Leu
1               5

<210> SEQ ID NO 71
<211> LENGTH: 9
<212> TYPE: PRT
<213> ORGANISM: Homo sapiens

<400> SEQUENCE: 71

Thr Leu Tyr Gly His Thr Phe Ala Val
1               5

<210> SEQ ID NO 72
<211> LENGTH: 9
<212> TYPE: PRT
<213> ORGANISM: Homo sapiens

<400> SEQUENCE: 72

Gln Leu Ala Thr Lys Ala Ala Arg Lys
1               5

<210> SEQ ID NO 73
<211> LENGTH: 9
<212> TYPE: PRT
<213> ORGANISM: Homo sapiens

<400> SEQUENCE: 73

Lys Ser Ala Pro Ser Thr Gly Gly Val
1               5

<210> SEQ ID NO 74
<211> LENGTH: 9
<212> TYPE: PRT
<213> ORGANISM: Homo sapiens

<400> SEQUENCE: 74

Lys Phe Asp Asp Ala Gly Leu Ser Leu
1               5

<210> SEQ ID NO 75
<211> LENGTH: 9
<212> TYPE: PRT
<213> ORGANISM: Homo sapiens

<400> SEQUENCE: 75

Tyr Leu Ser Leu Tyr Leu Leu Leu Val
1               5

<210> SEQ ID NO 76
<211> LENGTH: 9
<212> TYPE: PRT
<213> ORGANISM: Homo sapiens

<400> SEQUENCE: 76

```
Phe Val Gln Gly Lys Asp Trp Gly Phe
1               5

<210> SEQ ID NO 77
<211> LENGTH: 9
<212> TYPE: PRT
<213> ORGANISM: Homo sapiens

<400> SEQUENCE: 77

Val Leu Tyr Asp Gln Pro Arg His Val
1               5
```